United States Patent [19]

Koppes et al.

[11] Patent Number: 4,756,777

[45] Date of Patent: Jul. 12, 1988

[54] BIS(2,2,2-FLUORODINITROETHOXY)-(1,1,1-FLUORODINITRO-2-PROPOXY)METHANE

[75] Inventors: William M. Koppes, Adelphi; Horst G. Adolph, Silver Spring, both of Md.

[73] Assignee: The United States of America as represent by the Secretary of the Navy, Washington, D.C.

[21] Appl. No.: 46,474

[22] Filed: Apr. 3, 1987

[51] Int. Cl.$^4$ .............................................. C06B 25/00
[52] U.S. Cl. ...................................... 149/88; 568/590
[58] Field of Search ........................... 149/88; 568/590

[56] References Cited

U.S. PATENT DOCUMENTS

| | | | |
|---|---|---|---|
| H181 | 12/1986 | Koppes et al. | 149/88 |
| H184 | 1/1987 | Koppes et al. | 568/590 |
| 4,062,897 | 12/1977 | Adolph | 568/590 |
| 4,332,744 | 6/1982 | Gilligan et al. | 149/88 |
| 4,411,837 | 10/1983 | Gilligan et al. | 149/88 |
| 4,449,000 | 5/1984 | Sitzmann et al. | 149/88 |
| 4,453,021 | 6/1984 | Adolph | 149/88 |
| 4,499,309 | 2/1985 | Sitzmann et al. | 149/88 |

*Primary Examiner*—Edward A. Miller
*Attorney, Agent, or Firm*—Kenneth E. Walden; Roger D. Johnson

[57] ABSTRACT

Bis(2-fluoro-2,2-dinitroethoxy)(1-fluoro-1,1-dinitro-2-propoxy)methane which is useful as an energetic co-plasticizer with bis(2-fluoro-2,2-dinitroethyl)formal in plastic-bonded explosives.

6 Claims, No Drawings

BIS(2,2,2-FLUORODINITROETHOXY)-(1,1,1-FLUORODINITRO-2-PROPOXY)METHANE

BACKGROUND OF THE INVENTION

This invention relates to plasticizers and more particularly to energetic plasticizers for plastic-bonded explosives.

Examples of energetic plasticizers which are currently used in plastic-bonded explosives (PBXs) are bis(2-fluoro-2, 2-dinitroethyl) formal (FEFO), butanetriol trinitrate (BTTN), and trimethylolethane trinitrate (TMETN). These compounds have various disadvantages. BTTN and TMETN have limited thermal stability. While FEFO has excellent thermal stability, it suffers from high volatility and toxicity; it also has a high melting point. It therefore would be desirable to minimize or overcome the disadvantages of FEFO while maintaining its energy density and thermal stability.

SUMMARY OF THE INVENTION

Accordingly, an object of this invention is to provide a new organic compound.

Another object of this invention is to provide a new energetic plasticizer for plastic-bonded explosives.

A further object of this invention is to provide an energetic plasticizer having a low melting point and low volatility.

Yet another object of this invention is to provide a new plasticizer having high energy content and high thermal stability.

These and other objects of this invention are achieved by providing bis(2-fluoro-2,2-dinitroethoxy)(1-fluoro-1,1-dinitro-2-propoxy) methane (M-FDNEOF), $CF(NO_2)_2CH(CH_3)OCH[OCH_2CF(NO_2)_2]_2$. Bis(2-fluoro-2,2-dinitroethoxy)(1-fluoro-1,1-dinitro-2-propoxy) methane is prepared by the following reaction sequence:

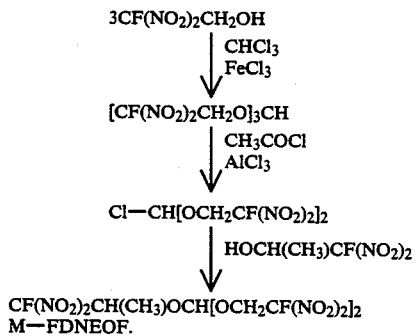

M-FDNEOF mixes in all ratios with FEFO to produce energetic plasticizers for plastic-bonded explosives.

DETAILED DESCRIPTION OF THE PREFERRED EMBODIMENT

Bis(2-fluoro-2,2-dinitroethoxy)(1-fluoro-1,1-dinitro-2-propoxy) methane (M-FDNEOF) is a new compound which has been found to act as an energetic coplasticizer for bis(2-fluoro-2,2-dinitroethyl) formal (FEFO) in combination with various energetic and non-energetic prepolymers commonly used in plastic-bonded explosive (PBX) formulations. M-FDNEOF is a low melting solid (mp 47°-9° C. ) with a calculated liquid density at 25° C. of 1.60g/cm$^3$. Its heat of formation is estimated to be $-314$ kcal/mol. M-FDNEOF is almost equal to FEFO in energy content (calculated detonation pressure, 243 kbar versus 248 kbar for FEFO). Therefore, the addition of M-FDNEOF to FEFO does not significantly change the energy content of the system. M-FDNEOF is miscible with FEFO in all proportions, and forms a binary eutectic with FEFO in the approximate weight ratio of FEFO:M-FDNEOF=70:30, mp 5° C. Thus the addition of M-FDNEOF, particularly in this amount, to FEFO results in a significant decrease of the plasticizer melting point; this will convey improved low-temperature properties to plastic-bonded explosives using the plasticizer mixture in place of FEFO alone. The volatility of M-FDNEOF was determined by thermogravimetric analysis (TGA) at 117° C. The weight loss was 0.003 mg/min., compared to 0.039 mg/min for FEFO. Thus, the volatility of M-FDNEOF is lower than that of FEFO by a factor of ten. The volatility of the plasticizer mixture will therefore be substantially lower than that of pure FEFO, and the volatility of FEFO will be reduced because of its reduced concentration. Note: M-FDNEOF will also form mixed plasticizers with other coplasticizers such as bis(2-fluoro-2,2-dinitroethyl)amine, BFDNA.

The energetic plasticizer mixture is made of from more than zero to less than 100, preferably from 20 to 50, more preferably from 25 to 40, and most preferably about 30 percent by weight of bis(2-fluoro-2,2-dinitroethoxy)(1-fluoro-1,1-dinitro-2-propoxy)methane (M-FDNEOF) with the remainder being bis(2-fluoro-2,2-dinitroethyl) formal (FEFO).

Bis(2-fluoro-2,2-dinitroethoxy)(1-fluoro-1,1-dinitro-2-propoxy) methane is prepared by the following reaction sequence:

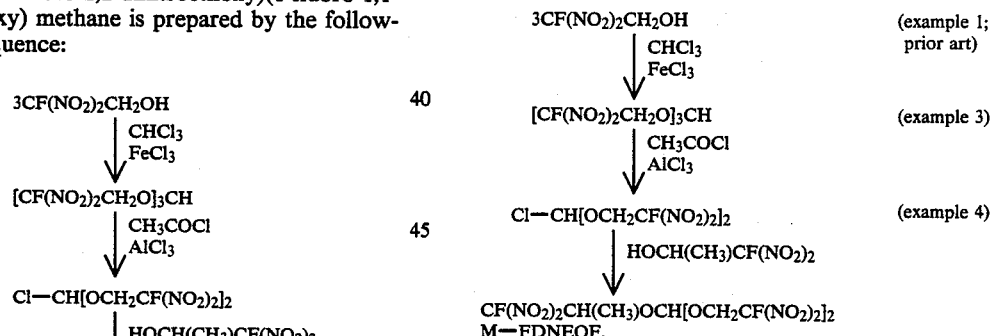

(Note that Example 2 illustrates the prior art preparation of $HOCH(CH_3)CF(NO_2)_2$ which is used in example 4.)

Bis(2-fluoro-2,2-dinitroethoxy)(1-fluoro-1,1-dinitro-2-propoxy) methane is prepared by reacting one mole of chloro bis(2-fluoro-2,2-dinitroethoxy)methane with one mole of 1-fluoro-1,1-dinitro-2-propanol under reflux conditions as described in Example 4.

The 1-fluoro-1,1-dinitro-2-propanol used in example 4 may be prepared according to the procedure described in example 2 (prior art).

The chloro bis(2-fluoro-2,2-dinitroethoxy)methane used in Example 4 was prepared by refluxing a solution of tris(2-fluoro-2,2-dinitroethoxy) methane, aluminum chloride, and acetyl chloride under the conditions described in Example 3.

The tris(2-fluoro-2,2-dinitroethoxy)methane used in example 3 was prepared by reacting 3 moles of 2-fluoro- 2,2-dinitroethanol with one mole of chloroform in the presence of anhydrous ferric chloride under the conditions disclosed in Example 1 (prior art).

The general nature of the invention having been set forth, the following examples are presented as specific illustrations thereof. It will be understood that the invention is not limited to these specific examples but is susceptible to various modifications that will be recognized by one of ordinary skill in the art.

EXAMPLES

Examples 1 and 2 are quoted from prior art sources to illlustrate methods of preparing certain starting materials.

Example 1 is incorporated from U.S. Pat. No. 3,388,147 entitled "2-Fluoro-2,2-dinitroethyl Carbonates and Production Thereof," which issued on June 11, 1968 to Mortimer J. Kamlet et al. (see col. 3, lines 22–36).

EXAMPLE 1

(Prior art)

tris(2-fluoro-2,2-dinitroethyl)orthoformate

"A mixture of 0.5 g. anhydrous ferric chloride and 10 ml. chloroform was placed in a 30 ml. round-bottom flask fitted with a magnetic stirrer and a reflux condenser connected through a bubbler to a methanol gas trap. 2-fluoro-2,2-dinitroethanol, 2.0 g. (0.013 mole) was added and the mixture stirred and refluxed for 24 hours, after which time the mixture was cooled to room temperature and the solvent removed in vacuo."

"The residue was drowned in iced water, stirred until the ferric chloride dissolved and the crystalline product collected. Recrystallization of this material from chloroform-hexane gave 1.38 g. (68%) pure tris(2-fluoro-2,2-dinitroethyl)orthoformate (FDNEOF) as fine colorless needles, M.P. 110–111.2°."

Example 2 is incorporated from Adolph, Horst G., "Fluoronitroaliphatics. V. Carbonyl Additions of Fluorodinitromethane," *Journal of Organic Chemistry*, vol. 35, no. 9, 1970, page 3188+, at page 3189, bottom of column 2.

EXAMPLE 2

1-fluoro-1,1-dinitro-2-propanol

"1-fluoro-1,1-dinitropropanol-2. A 38% aqueous solution of acetaldehyde, 5.2 g, was added to a well-stirred and cooled mixture of 3.7 g of fluorodinitromethane and 5 ml of water. A few drops of saturated sodium bicarbonate solution was added and the mixture stirred with continued cooling for 1 hr. It was then acidified with dilute sulfuric acid, the product extracted into methylene chloride, and the extract dried and distilled. Obtained was 4 g (79%), bp 40°–42° (0.5 mm)."

Examples 3 and 4 illustrate the preparation of the compounds of this invention.

EXAMPLE 3 chloro bis(2-fluoro-2,2-dinitroethoxy)methane

A solution of tris(2-fluoro-2,2-dinitroethoxy)methane (23.6 g, 0.050 mol), aluminum chloride (12.0 g, 0.090 mol) and acetyl chloride (200 g) was refluxed for 1.5 hours and then concentrated on a rotary evaporator to a viscous liquid. This was extracted with chloroform ($2 \times 50$ ml). After treatment with activated charcoal (2 g), this solution was filtered and concentrated (rot. evap., 40° bath) to 23 g of residue from which 8.53 g (87%) of fluorodinitroethyl acetate (bp 40-3° /0.1 mm) was removed by distillation. The residual liquid (14.14 g, 80% yield) was chloro bis(2-fluoro-2,2-dinitroethoxy)methane free of contaminants by $^1$H NMR analysis.

Anal. Calcd for $C_5H_5ClF_2N_4O_{10}$: C, 16.94; H, 1.42; Cl, 10.00; F, N, 15.42.

EXAMPLE 4 bis(2-fluoro-2,2-dinitroethoxy)(1-fluoro-1,1-dinitro-2-propoxy)methane

The chloroformal of Example 3, 3.54 g (0.010 mol), was refluxed with 1.68 g (0.010 mol) of 1-fluoro-1,1-dinitro-2-propanol in 10 ml of dichloroethane for 6 hours. Volatiles were removed on a rotary evaporator at aspirator pressure, then at 0.25 mm (110° C. bath) to give a dark red liquid residue. Filtration of a dichloromethane solution (50 ml) of this material through silica gel (3 g) gave 3.81 g of yellow liquid, which crystallized on standing. $^1$H NMR analysis showed the solid to be a mixture of 0.4 g of tris(2-fluoro-2,2-dinitroethoxy)methane and 3.4 g (70%) of bis(2-fluoro-2,2-dinitroethoxy)(1-fluoro-1,1-dinitro-2-propoxy)methane. Recrystallization from chloroform provided pure bis(2-fluoro-2,2-dinitroethoxy)(1-fluoro-1,1-dinitro-2-propoxy)methane; m.p. 47–9° C.; $^1$H NMR (CDCl$_3$) $\delta$5.69 (s, 1), 5.30 (d of q, 1, J=18 Hz, 6 Hz), 4.73 (d, 4, J=15 Hz), 1.50 (d, 3, J=6 Hz). Anal. Calcd for $C_8H_9F_3N_6O_{15}$: C, 19.76; H, 1.87; F, 11.72; N, 17.29. Found: C, 19.71; H, 1.82; F, 11.81; N, 16.95.

Obviously numerous modifications and variations of the present invention are possible in light of the above teachings. It is therefore to be understood that within the scope of the appended claims the invention may be practiced otherwise than as specifically described herein.

What is claimed as new and desired to be secured by Letters Patent of the United States is:

1. Bis(2-fluoro-2,2-dinitroethoxy)(1-fluoro-1,1-dinitro-2-propoxy) methane.

2. Chloro bis(2-fluoro-2,2-dinitroethoxy)methane.

3. A mixture comprising essentially from more than zero to less than 100 weight percent of bis(2-fluoro-2,2-dinitroethoxy) (1-fluoro-1,1-dinitro-2-propoxy)methane with bis (2-fluoro-2,2-dinitroethyl) formal being the remainder of the mixture.

4. The mixture of claim 3 comprising essentially from 20 to 50 weight percent of bis(2-fluoro-2,2-dinitroethoxy)(1-fluoro-1,1-dinitro-2-propoxy) methane with bis(2-fluoro-2,2-dinitroethyl) formal being the remainder.

5. The mixture of claim 4 comprising essentially from 25 to 40 weight percent of bis(2-fluoro-2,2-dinitroethoxy)(1-fluoro-1,1-dinitro-2-propoxy) methane with bis(2-fluoro-2,2-dinitroethyl) formal being the remainder.

6. The mixture of claim 5 comprising essentially about 30 weight percent of bis(2-fluoro-2,2-dinitroethoxy)(1-fluoro-1,1-dinitro-2-propoxy) methane and about 70 weight percent of bis(2-fluoro-2,2-dinitroethyl) formal.

* * * * *